(12) United States Patent
Bader et al.

(10) Patent No.: US 11,439,414 B2
(45) Date of Patent: Sep. 13, 2022

(54) MEDICAL INSTRUMENTARIUM COMPRISING SAWING TEMPLATE

(71) Applicant: Aesculap AG, Tuttlingen (DE)

(72) Inventors: Uwe Bader, Tuttlingen (DE); Anil Varsani, Tuttlingen/Moehringen (DE); Stephanie Stoll, Herrenzimmern (DE)

(73) Assignee: Aesculap AG, Tuttlingen (DE)

( * ) Notice: Subject to any disclaimer, the term of this patent is extended or adjusted under 35 U.S.C. 154(b) by 203 days.

(21) Appl. No.: 16/516,354

(22) Filed: Jul. 19, 2019

(65) Prior Publication Data

US 2019/0336145 A1 Nov. 7, 2019

Related U.S. Application Data

(63) Continuation of application No. PCT/EP2018/051371, filed on Jan. 22, 2018.

(30) Foreign Application Priority Data

Jan. 20, 2017 (DE) .................... 10 2017 101 135.8

(51) Int. Cl.
  *A61B 17/17* (2006.01)
  *A61B 17/16* (2006.01)
  *A61F 2/46* (2006.01)

(52) U.S. Cl.
  CPC ...... *A61B 17/1742* (2013.01); *A61B 17/1659* (2013.01); *A61B 17/1664* (2013.01); *A61F 2/4603* (2013.01); *A61F 2250/0097* (2013.01)

(58) Field of Classification Search
  CPC . A61B 17/1742; A61B 17/15; A61B 17/1668; A61B 17/164
  See application file for complete search history.

(56) References Cited

U.S. PATENT DOCUMENTS

| 6,206,884 B1 | 3/2001 | Masini |
| 6,224,605 B1 | 5/2001 | Anderson et al. |
| 6,395,004 B1 * | 5/2002 | Dye ................. A61B 17/164 606/86 R |
| 2011/0160733 A1 | 6/2011 | Wallstein et al. |
| 2012/0130500 A1 | 5/2012 | Maroney et al. |

FOREIGN PATENT DOCUMENTS

| DE | 202010000184 | 7/2010 |
| EP | 3095419 | 11/2016 |
| FR | 2854786 | 11/2004 |
| FR | 2997621 | 5/2014 |
| JP | 2010540123 | 12/2010 |
| JP | 2013-126545 | 6/2013 |
| JP | 2015516220 | 6/2015 |
| JP | 2015154951 | 8/2015 |
| WO | 2005110250 | 11/2005 |
| WO | 2009045960 | 4/2009 |
| WO | 2013160674 | 10/2013 |
| WO | 2014152535 | 9/2014 |

* cited by examiner

*Primary Examiner* — Andrew Yang
(74) *Attorney, Agent, or Firm* — Lipsitz & McAllister, LLC

(57) ABSTRACT

The invention relates to a medical instrumentarium for implanting a hip joint endoprosthesis, which instrumentarium comprises at least one sawing template with at least one guide slot for a saw blade, wherein the sawing template comprises at least one first coupling element for temporarily coupling the sawing template to a second coupling element of a rasp body of a prosthesis rasp in a coupling position.

30 Claims, 11 Drawing Sheets

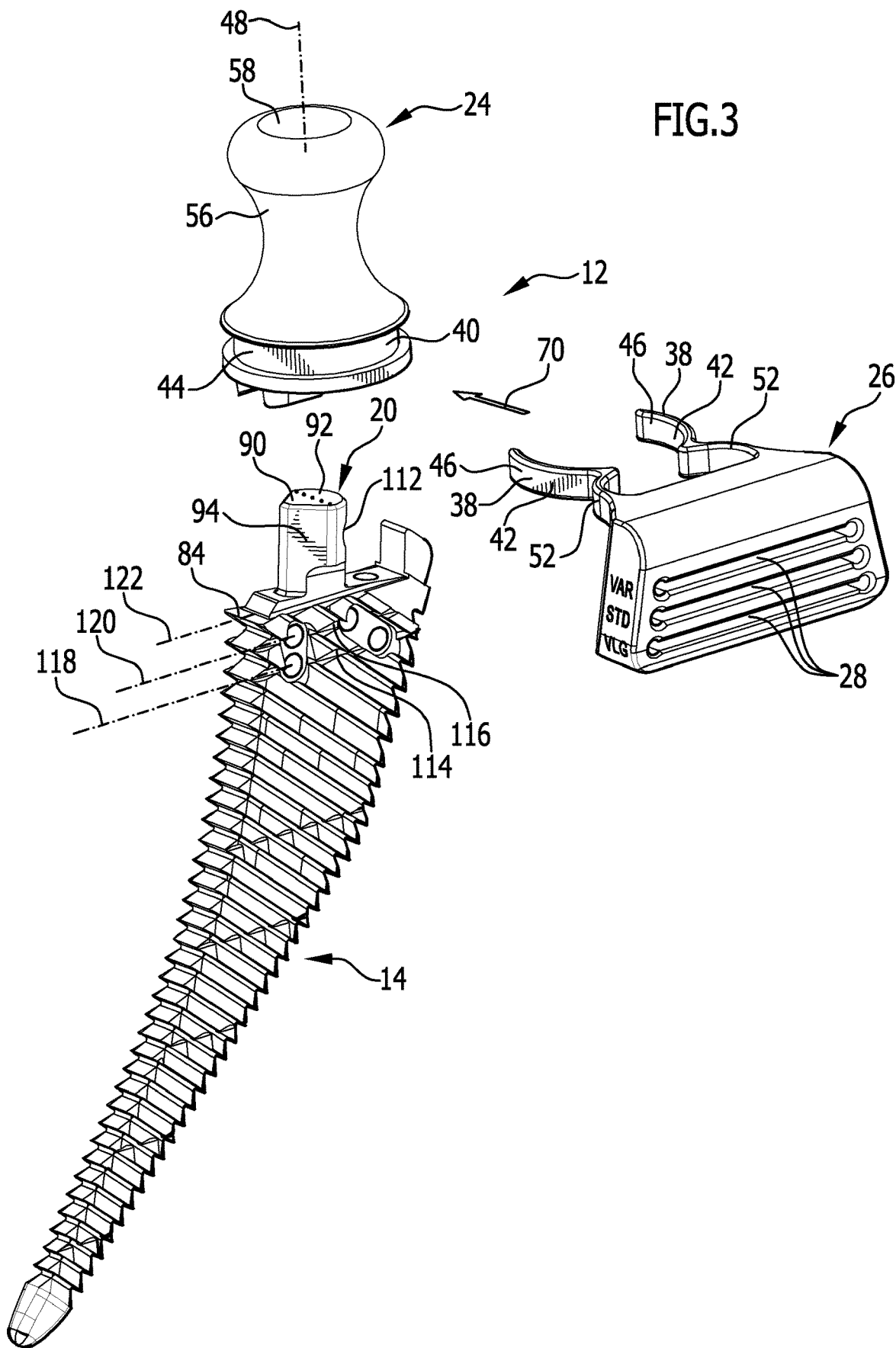

Figure 1:
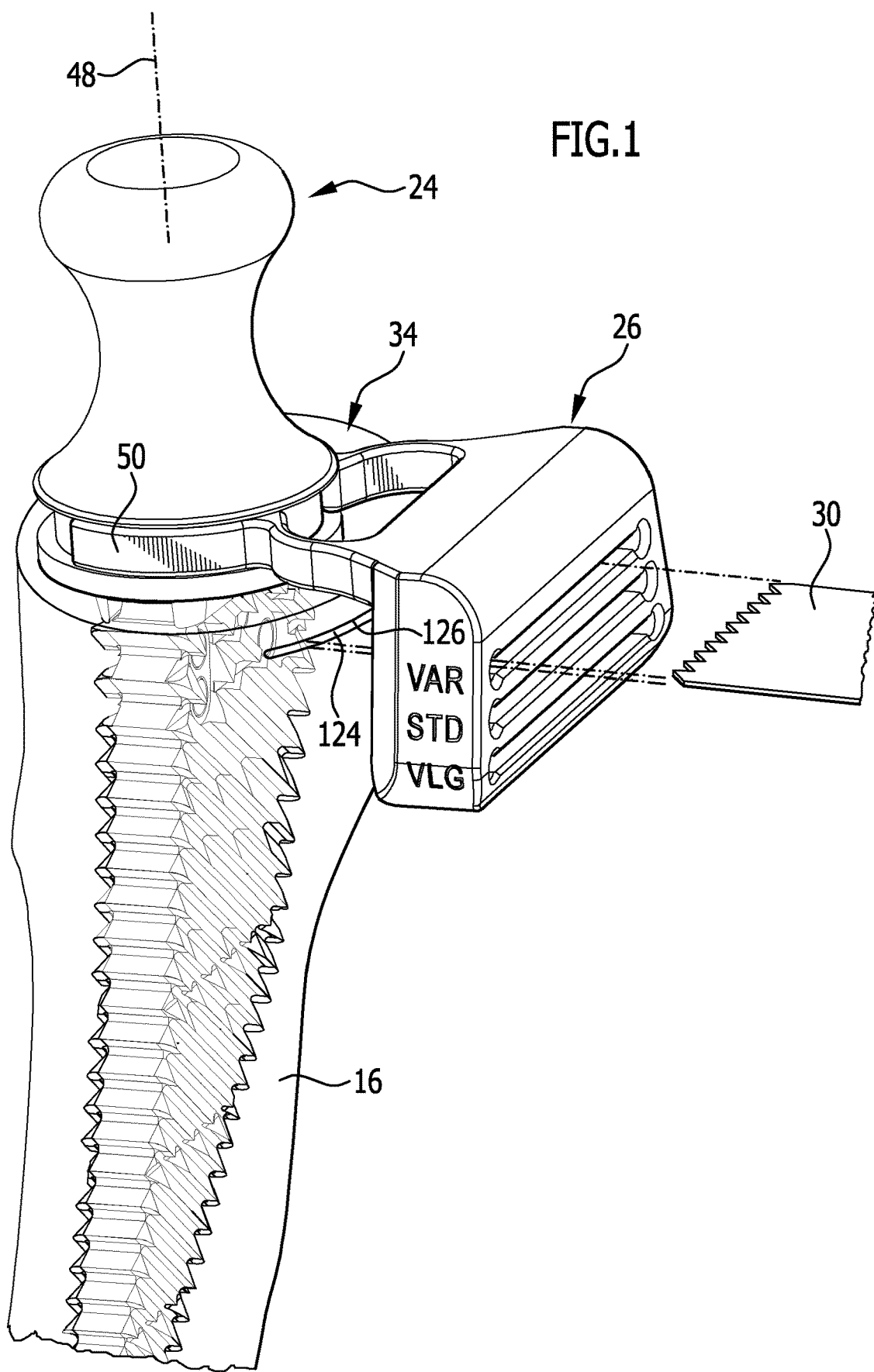

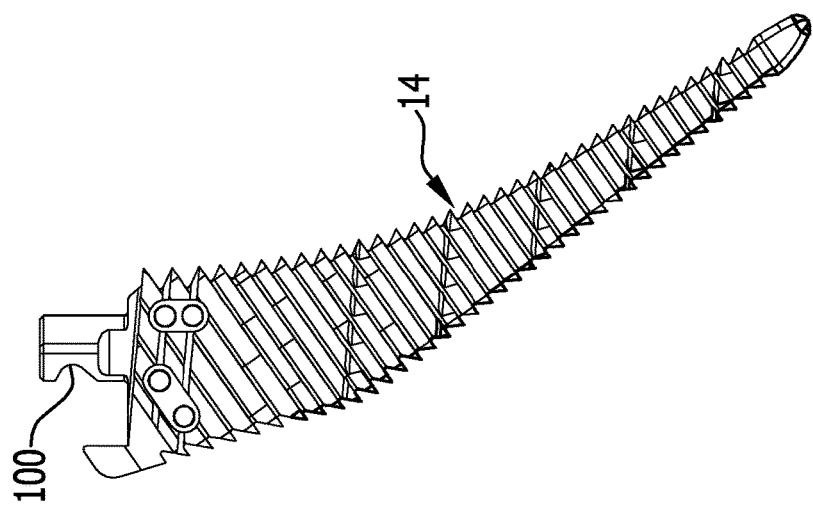
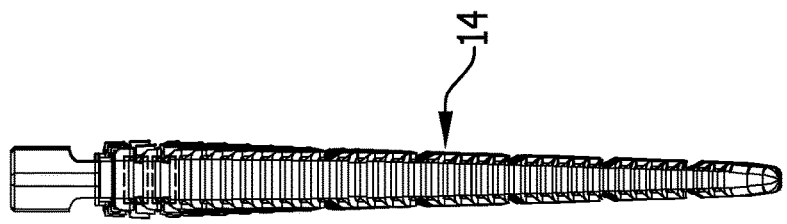
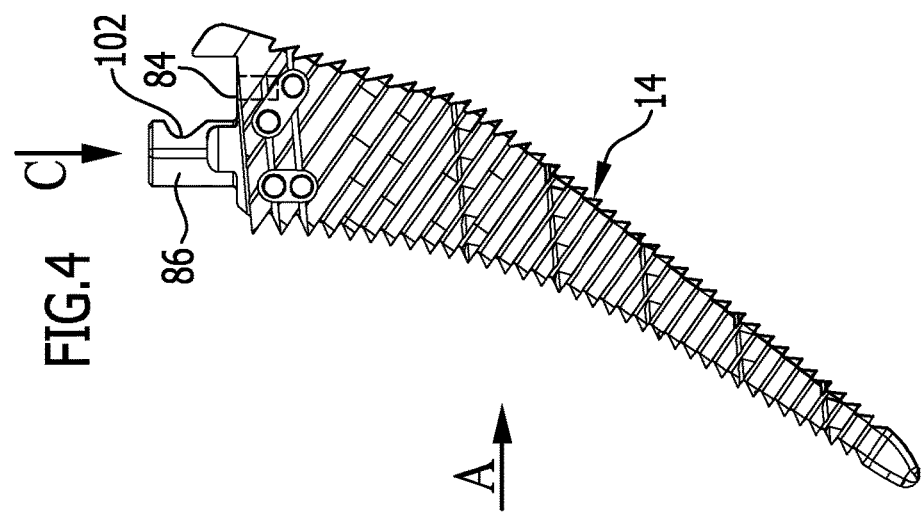
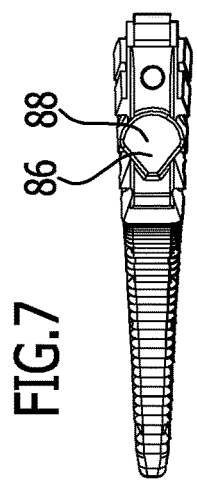

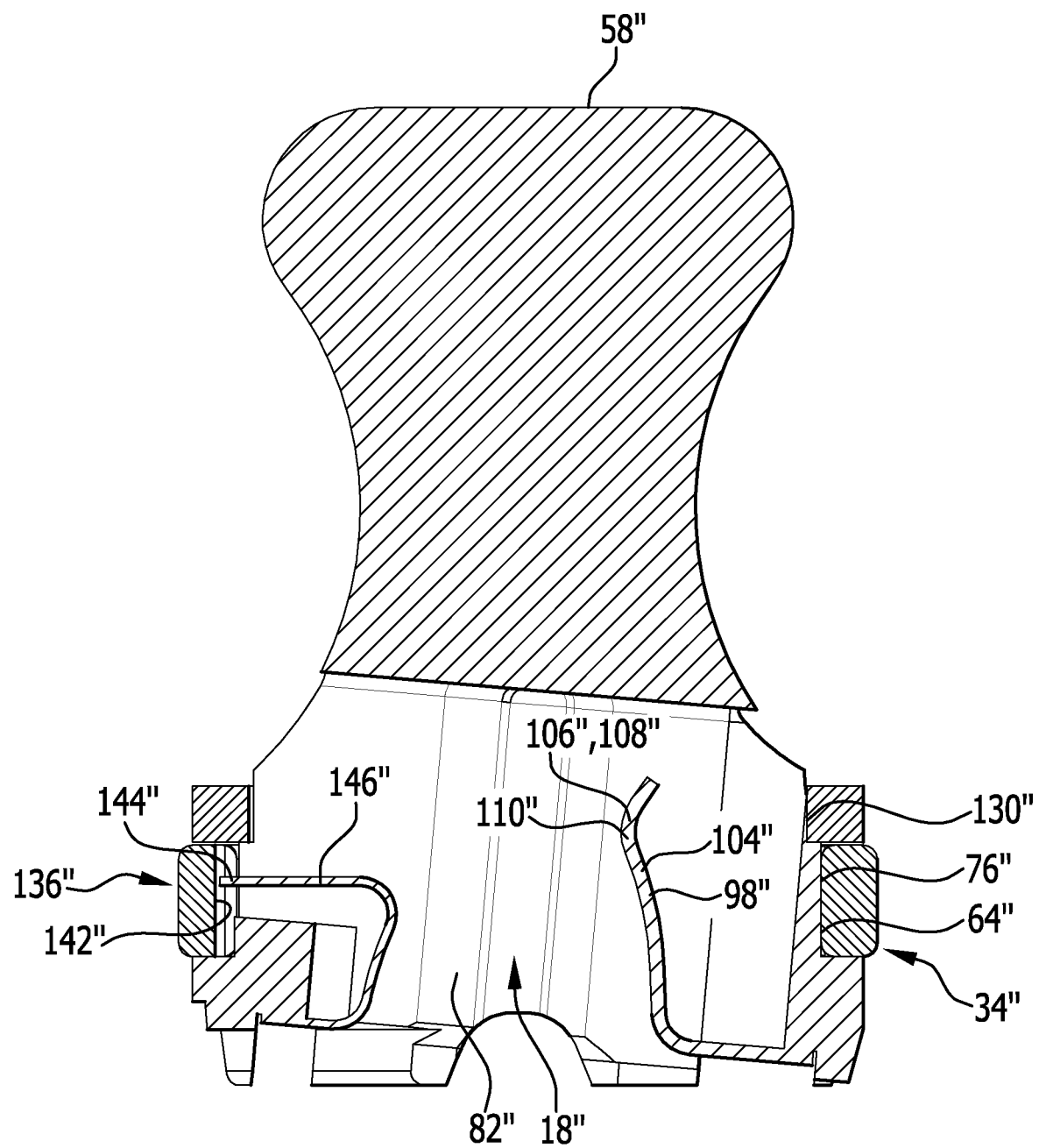

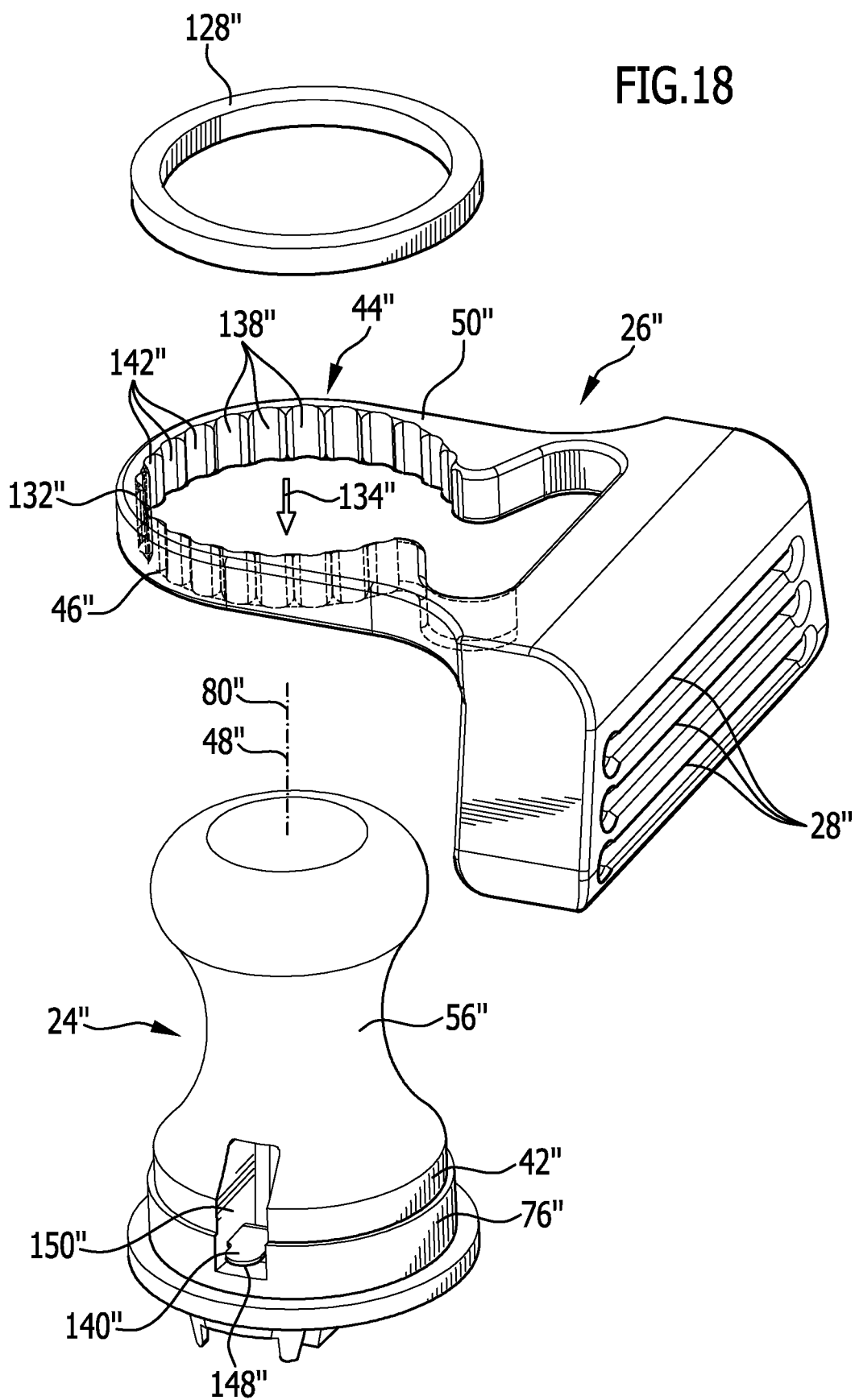

MEDICAL INSTRUMENTARIUM COMPRISING SAWING TEMPLATE

CROSS-REFERENCE TO RELATED APPLICATIONS

This application is a continuation of international application number PCT/EP2018/051371 filed on Jan. 22, 2018 and claims the benefit of German application number 10 2017 101 135.8 filed on Jan. 20, 2017, which are incorporated herein by reference in their entirety and for all purposes.

FIELD OF THE INVENTION

The present invention relates to medical instrumentariums for implanting a hip joint endoprosthesis generally, and more specifically to a medical instrumentarium for implanting a hip joint endoprosthesis, which instrumentarium comprises at least one sawing template with at least one guide slot for a saw blade.

BACKGROUND OF THE INVENTION

Damaged hip joints have been replaced by hip joint endoprostheses for many years. A prosthesis stem which is inserted into a femoral cavity prepared therefor forms a part of such hip joint endoprostheses. Arranged on the prosthesis stem is a joint ball which, together with a joint socket anchored in the pelvis of the patient, forms a ball-and-socket joint.

Prosthesis stems of hip joint endoprostheses are anchored in the femur, in particular without cement. It is hereby desirable if the femur is resected in the region of the neck of the femur such that it optimally meets with an end of the prosthesis stem protruding out of the femur bone.

Such a resection may be performed with a sawing template, for example. Though because they have no fixedly predetermined reference on the femur, larger angular errors and an offset of the resection height frequently occur when they are used. In other words, too much or too little is removed from the femur bone, so that a proximal end of the femur does not end as desired in the proximal end region of the prosthesis stem.

SUMMARY OF THE INVENTION

In a first aspect of the invention, a medical instrumentarium for implanting a hip joint endoprosthesis is provided. Said instrumentarium comprises at least one sawing template with at least one guide slot for a saw blade. The sawing template comprises at least one first coupling element for temporarily coupling the sawing template to a second coupling element of a rasp body of a prosthesis rasp in a coupling position.

BRIEF DESCRIPTION OF THE DRAWING FIGURES

Figure 2:
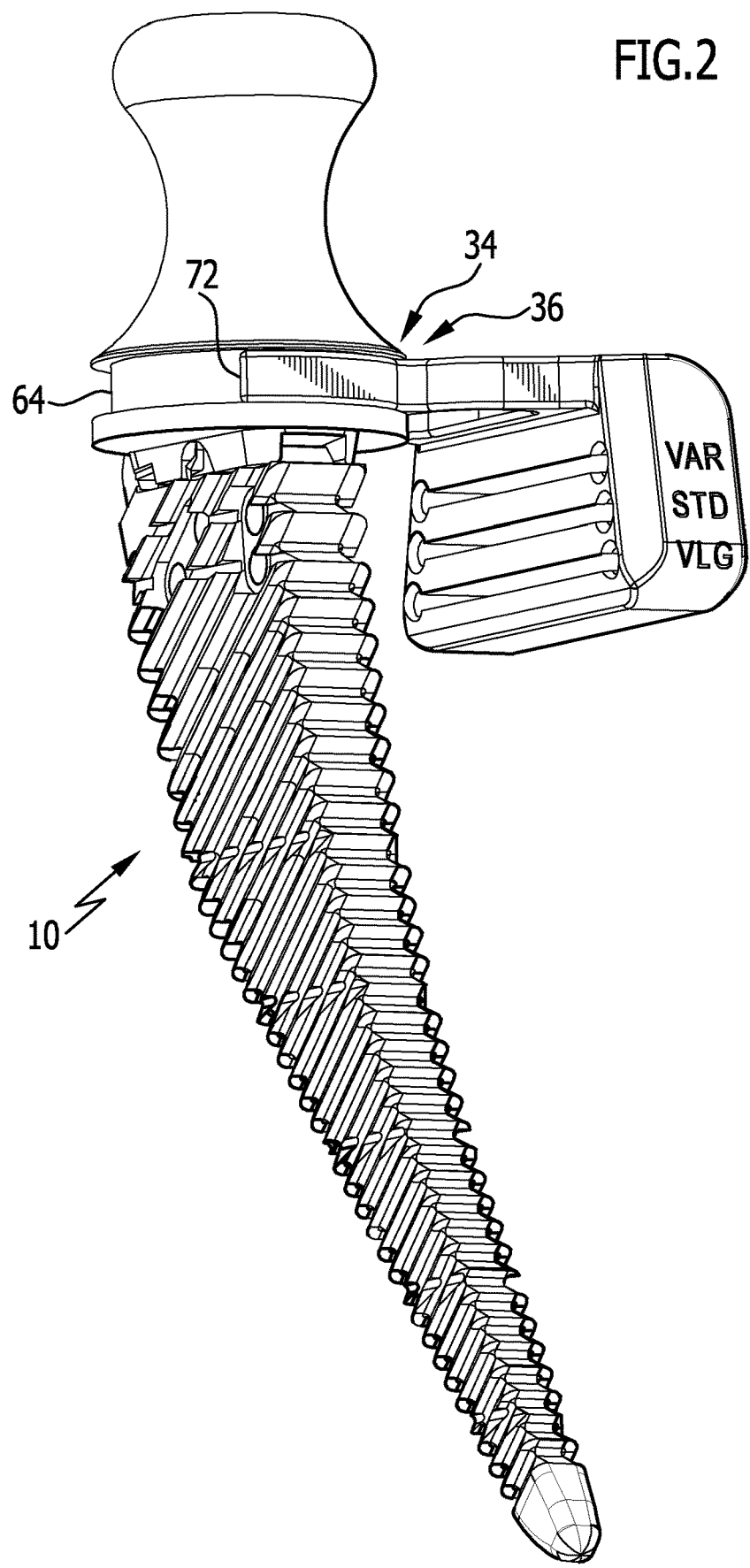
Figure 8:
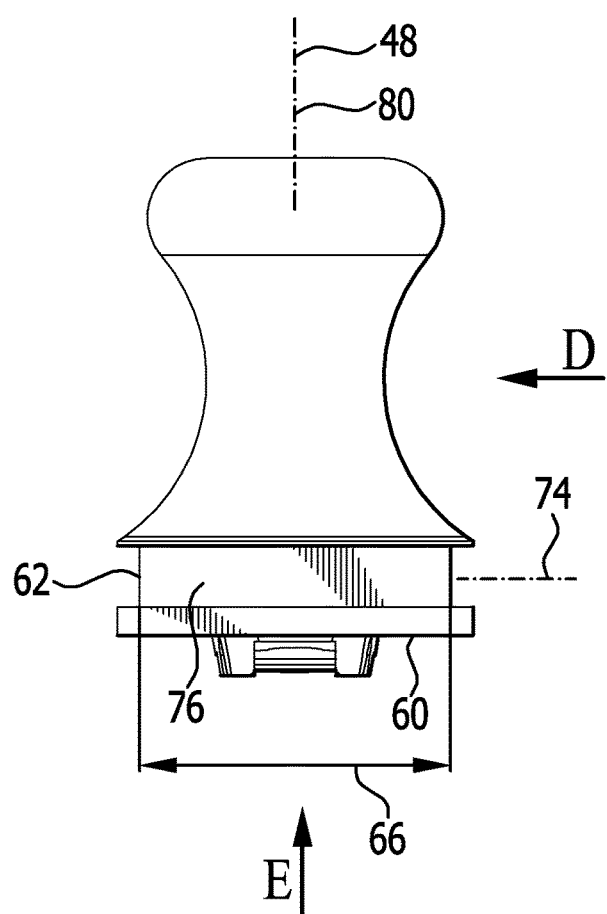
Figure 9:
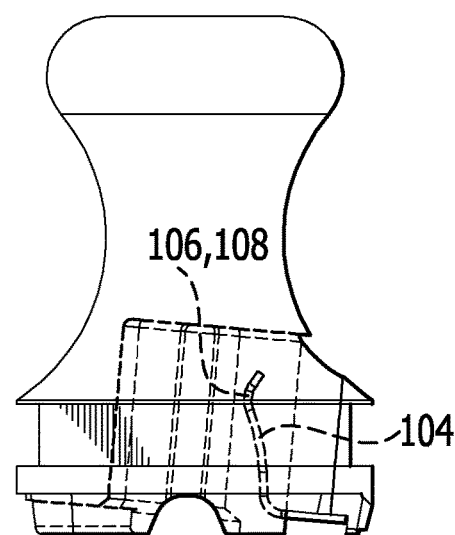
Figure 10:
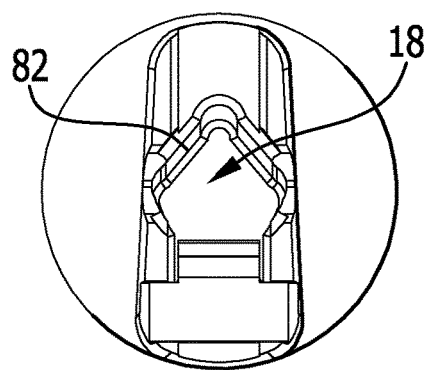
Figure 11:
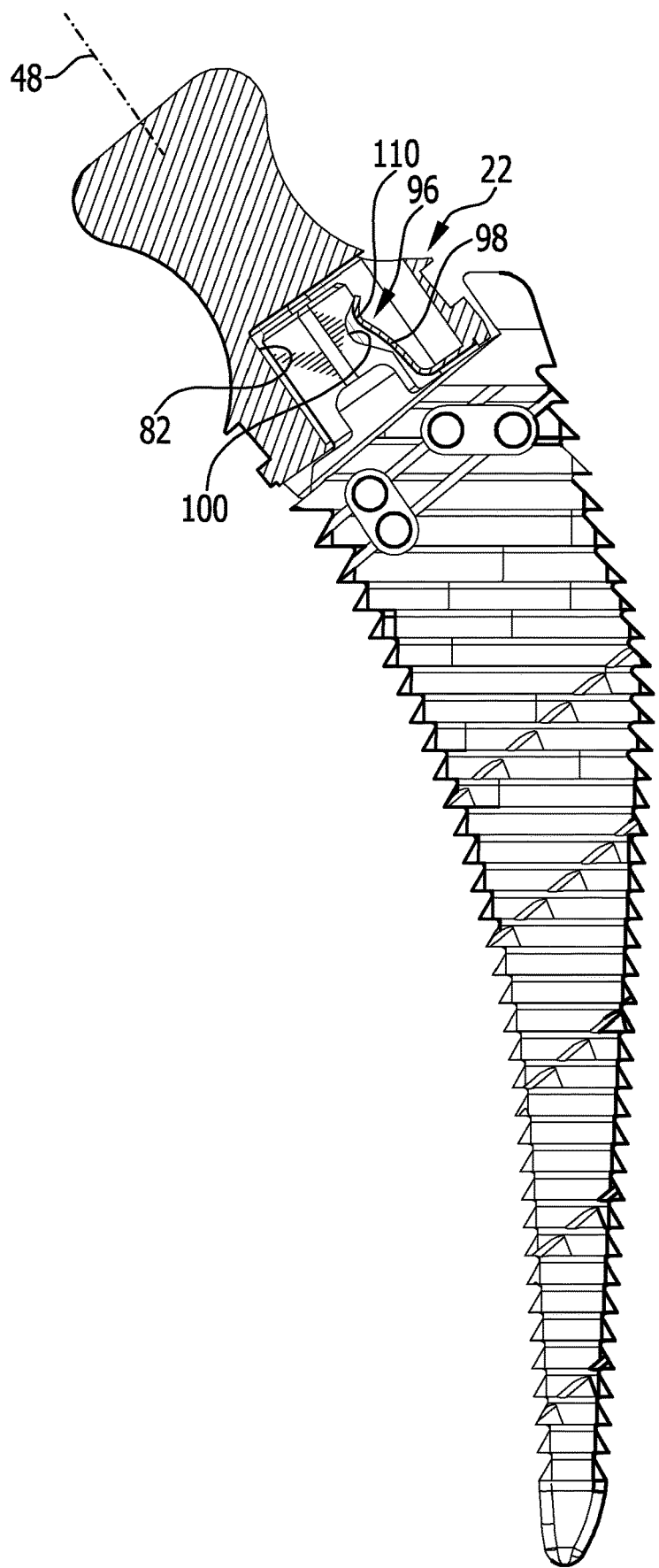
Figure 12:
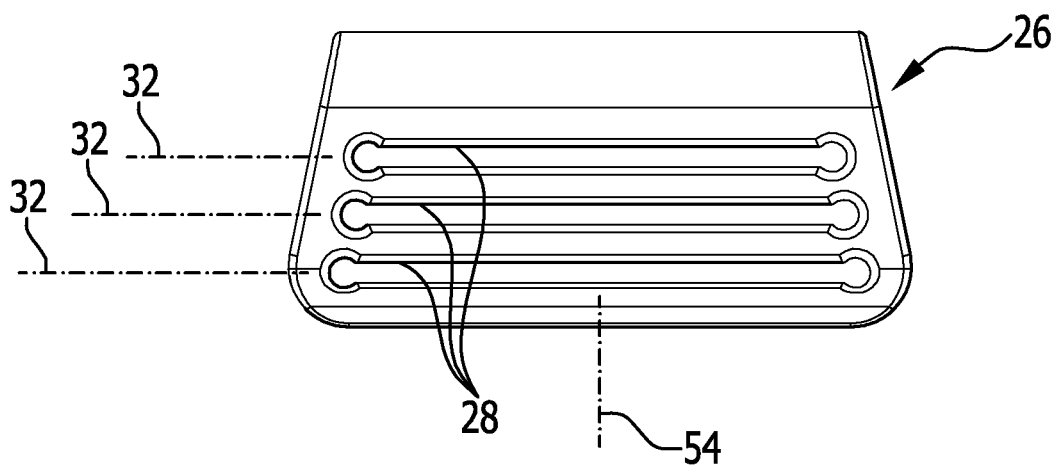
Figure 13:
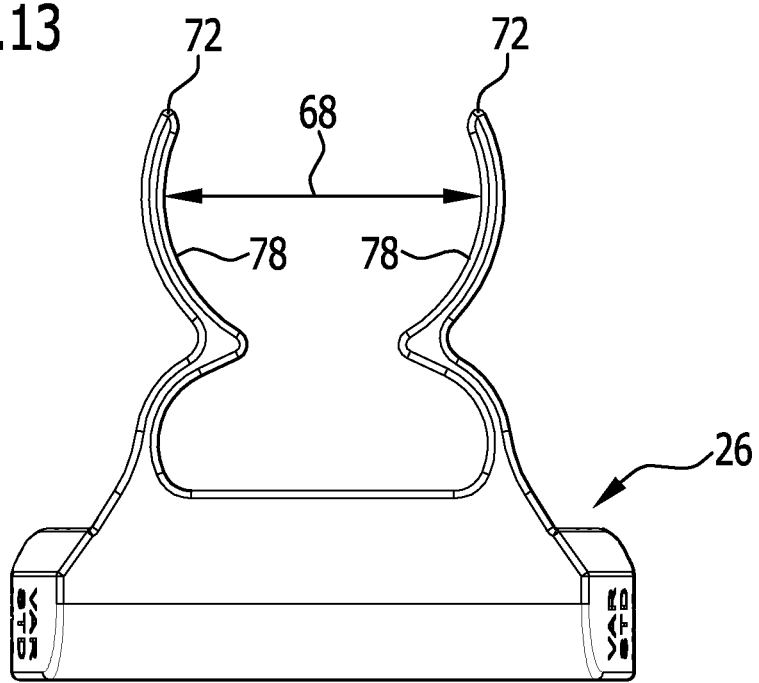
Figure 14:
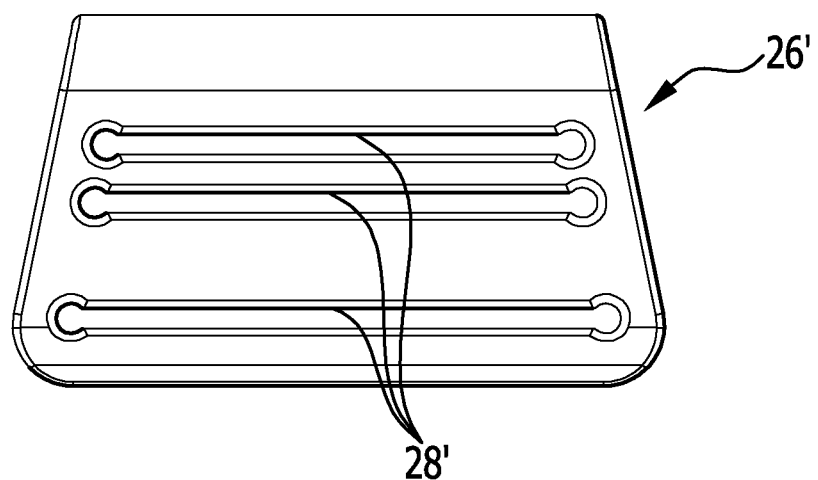
Figure 15:
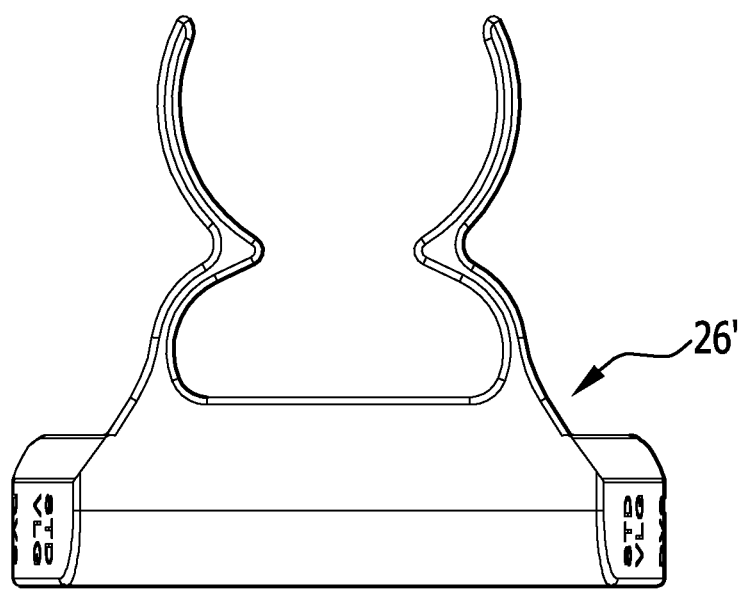
Figure 16:
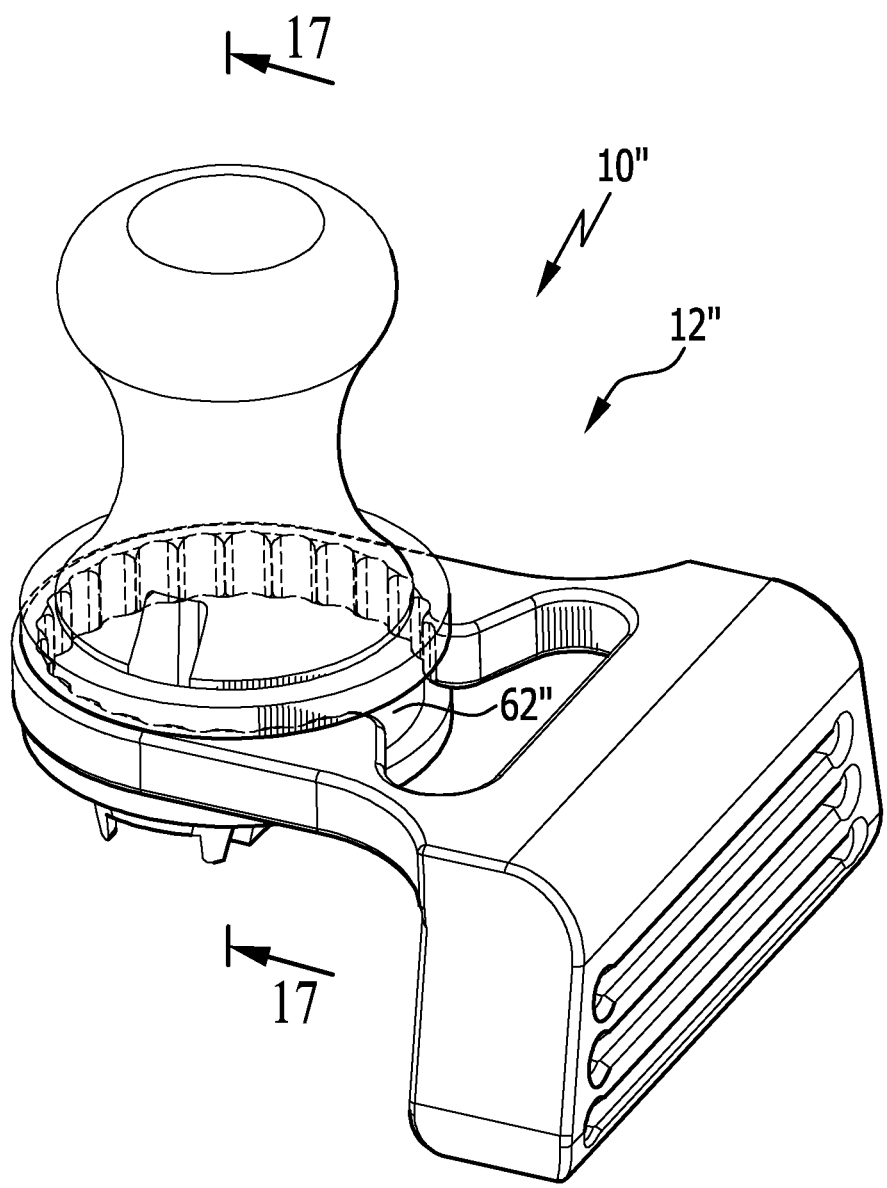

The foregoing summary and the following description may be better understood in conjunction with the drawing figures, of which:

FIG. 1: shows a perspective view of a first embodiment of a medical instrumentarium in accordance with the invention;

FIG. 2: shows a further perspective total view of the medical instrumentarium from FIG. 1;

FIG. 3: shows an exploded depiction of the arrangement from FIG. 2;

FIG. 4: shows a side view of the rasp body of the instrumentarium from FIGS. 1 to 3;

FIG. 5: shows a view of the rasp body from FIG. 4 in the direction of the arrow A;

FIG. 6: shows a side view of the rasp body from FIG. 5 in the direction of the arrow B;

FIG. 7: shows a view of the rasp body from FIG. 4 in the direction of the arrow C;

FIG. 8: shows a side view of the coupling body of the instrumentarium from FIGS. 1 to 3;

FIG. 9: shows a partially broken side view of the coupling body from FIG. 8;

FIG. 10: shows a view of the coupling body from FIG. 8 in the direction of the arrow E;

FIG. 11: shows a side view of the rasp body similar to FIG. 4 with a coupled coupling body in a longitudinal sectional view;

FIG. 12: shows a side view of the template body from FIGS. 1 to 3;

FIG. 13: shows a plan view of the template body from FIG. 12 in the direction of the arrow F;

FIG. 14: shows a side view of a second embodiment of a template body;

FIG. 15: shows a plan view of the template body from FIG. 14 in the direction of the arrow G;

FIG. 16: shows a schematic perspective and partially broken total view of a second embodiment of a sawing template;

FIG. 17: shows a sectional view along the line 17-17 in FIG. 16; and FIG. 18: shows an exploded depiction of the sawing template from FIG. 16.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical instrumentarium for implanting a hip joint endoprosthesis, which instrumentarium comprises at least one sawing template with at least one guide slot for a saw blade, wherein the sawing template comprises at least one first coupling element for temporarily coupling the sawing template to a second coupling element of a rasp body of a prosthesis rasp in a coupling position.

The solution proposed in accordance with the invention makes it possible to couple, in particular in a simple manner, the sawing template, for example in a defined manner, to a rasp body of a prosthesis rasp in the coupling position. A prosthesis rasp is used to prepare the bone cavity on the femur bone of the patient, in order to prepare the bone cavity in such a way that the prosthesis stem to ultimately be implanted sits perfectly in the femoral cavity. This is important in particular if the prosthesis stem is anchored in a cement-free manner. The prosthesis stem may in particular have an osteointegrative coating which facilitates the ingrowing of bone. Thus the prosthesis stem held in the bone cavity only by clamping fit may be permanently connected securely to the femur bone. Because the rasp body of the prosthesis rasp corresponds in its outer contour to the prosthesis stem to be implanted, the final position of the prosthesis stem in the femur bone is thus also known, namely through the rasp body driven into the femoral cavity. Said rasp body may then form a reference for the sawing template relative to the femur bone. The second coupling element on the sawing template thus enables in particular a defined connection to the rasp body, so that the femur bone is able to be partially resected in a desired manner by using the sawing template, namely corresponding to a proximal end of the prosthesis stem to be implanted or to a proximal end line of the osteointegrative coating on the prosthesis stem to be implanted. For this purpose, a saw blade may be guided in a defined manner by the at least one guide slot of the sawing template, which is coupled to the rasp body of the prosthesis rasp.

It is favorable if the sawing template comprises a coupling body and a template body, and if the at least one coupling element is arranged or formed on the coupling body, and if the at least one guide slot is arranged or formed on the template body. In particular, the coupling body and the template body may be formed as one piece or be permanently connected to each other, for example by bonding, welding, soldering or the like.

It is advantageous if the instrumentarium comprises a coupling device for temporarily coupling the coupling body and the template body in a coupling position. The coupling device makes it possible in particular to temporarily couple the coupling body and the template body to each other in the coupling position in a force- and/or positive-locking manner. Thus the template body may be separated from the coupling body in a simple manner and reconnected thereto as necessary. Thus in particular a cleanability of the instrumentarium is improved. In addition, the instrumentarium may optionally also be of modular configuration. For example, different template bodies may be brought into engagement with the same coupling body in order to partially resect the femur bone of the patient. In this case, in particular different rasp bodies may each be associated with a specific template body in order to thus be able to specify a defined reference for a surgeon to process the femur.

The coupling body and the template body may be coupled to each other in a simple manner if the coupling device is configured in the form of a latching or snapping connecting device and comprises latching or snapping elements which are in engagement with each other in the coupling position.

It is favorable if the coupling device comprises first and second coupling elements, if the first and second coupling elements are arranged or formed on the coupling body on the one hand and on the template body on the other hand, and if the first and second coupling elements in the coupling position are in engagement in a force- and/or positive-locking manner. By bringing the first and second coupling elements into engagement, the coupling body and the template body may thus be temporarily connected to each other in a simple manner.

The first and second coupling elements advantageously form the latching or snapping elements. The coupling device may thus be configured in a simple manner.

In accordance with a further preferred embodiment, provision may be made for the coupling body and the template body in the coupling position to be mounted on each other so as to be rotatable relative to each other about a rotary axis defined by the coupling device. This embodiment makes it possible in particular to couple the coupling body and the template body in a defined manner, for example in a direction specified by the rotary axis. However, at the same time, a rotation of the coupling body and the template body relative to each other may also be made possible. Thus the template body may be aligned in particular in a desired manner in order to process the femur bone of the patient in a targeted manner. Such a possibility of rotation allows a surgeon to process the femur bone from different directions. Thus in particular the template body may be configured to be very small and compact.

The configuration of the coupling device is simplified further if the first and second coupling elements are configured in the form of at least one coupling projection and in the form of a corresponding coupling recess. For coupling the template body and the coupling body, the at least one coupling projection may thus be inserted into the corresponding coupling recess.

The at least one coupling projection is preferably resiliently arranged or formed on the template body. Alternatively, it may also be arranged or formed on the coupling body. The resilient configuration makes it possible in particular for the coupling projection to be able to snap into the corresponding coupling recess.

It is favorable if the at least one coupling projection is configured in the form of a mounting bracket which is concavely curved pointing toward the rotary axis. In particular, two or more coupling projections of that kind may be provided, which engage into an annular groove on the coupling body that faces away from the rotary axis and surrounds the same, in particular concentrically.

In order to achieve a secure connection between the template body and the coupling body, it is advantageous if the at least one coupling projection is configured in the form of a coupling ring which is closed in itself or extends over at least 180° in circumferential direction in relation to the rotary axis. In this way, the coupling body and the template body may be coupled easily and securely. In addition, a rotation of the coupling body and the template body relative to each other about the rotary axis may thus optionally also be made possible in a simple manner.

The instrumentarium may be configured particularly compactly if the at least one coupling recess is configured in the form of an annular groove which is open pointing away from the rotary axis and if the at least one coupling projection in the coupling position engages at least in sections into the coupling recess in circumferential direction in relation to the rotary axis. In particular, two or more coupling projections may be provided, which in the coupling position engage into the annular groove. In particular, coupling projections may be configured in a form which makes it possible to be able to snap or latch the coupling projections into the annular groove.

It is advantageous if the annular groove is laterally delimited by a retaining ring. Thus the annular groove, for one, may be produced in a simple manner. For another, a coupling ring closed in itself may optionally also be secured in the annular groove with the retaining ring. The retaining ring may optionally be permanently or temporarily arranged or formed on the coupling recess.

It is favorable if the retaining ring and the coupling body are connected to each other in a force- and positive-locking manner and/or by material bond. Thus in particular the template body may remain permanently coupled to the coupling body.

As described above, it is optionally possible to rotate the coupling body and the template body relative to each other about the rotary axis. It may hereby be favorable in particular if the first and second coupling elements are alignable relative to each other in discrete angular positions in relation to the rotary axis. In particular, a plurality of discrete angular positions may be provided here. Thus in particular the template body may be aligned relative to the coupling body in a desired manner.

In accordance with a further preferred embodiment, provision may be made for the instrumentarium to comprise an angle adjusting device for adjusting an angular position of the coupling body and the template body relative to each other in relation to the rotary axis. The angle adjusting device makes it possible in particular to align the template body and the coupling body relative to each other in relation to the rotary axis in a desired manner.

It is favorable if the angle adjusting device comprises a plurality of first angle adjusting members and at least one second angle adjusting member, and if the at least one second angle adjusting member is in engagement with different first angle adjusting members in different angular positions. For example, the at least one second angle adjusting member may be configured to come into engagement in a latching manner with the plurality of first angle adjusting members in different angular positions.

The angle adjusting device may be configured in a simple manner if the plurality of first angle adjusting members are configured in the form of angle member recesses and if the at least one second angle adjusting member is configured in the form of an angle member projection. The plurality of first angle adjusting members may thus be configured in particular in the form of a row of teeth, wherein the at least one second angle adjusting member is able to dip between adjacent teeth of the row of teeth in different angular positions.

It is advantageous if the angle member recesses are arranged or formed on the first or second coupling element and are arranged or formed pointing in the direction toward the rotary axis or away from the rotary axis. Thus the template body may be aligned relative to the coupling body in defined angular positions in a simple manner.

It is favorable if the at least one angle member projection is resiliently mounted and, when changing the angular position by rotating the first and second coupling elements relative to each other about the rotary axis, is moved out of one of the angle member recesses counter to a biasing force and in another angular position is moved back into one of the angle member recesses as a result of the biasing force. This configuration enables a surgeon to change an angular position between the template body and the coupling body, which is defined by the angle adjusting device, by simply rotating the template body and the coupling body relative to each other.

It is advantageous if the at least one guide slot defines a guidance plane which runs transversely to the rotary axis. In particular, the guidance plane may run perpendicularly to the rotary axis. Optionally, the template body may have two, three, or more guide slots which are associated with different prosthesis stems. Thus a surgeon is able to resect with one single template body a femur bone in a desired manner in dependence on the prosthesis stem to be implanted. In this way, the number of template bodies required may be significantly minimized.

The instrumentarium may be handled in a simple manner if the coupling body defines a grip region. The surgeon may grip the coupling body at said region and thus bring it into engagement with the rasp body, for example.

The instrumentarium may be configured in a simple and inexpensive manner, for example by the grip region being formed symmetrically in relation to the rotary axis. In particular, it may be formed rotationally symmetrically in relation to the rotary axis.

In accordance with a further preferred embodiment, provision may be made for the medical instrumentarium to comprise a rasp body of a prosthesis rasp, which rasp body comprises a second coupling element of a coupling device comprising the first and the second coupling element. In particular, the first and the second coupling element may be formed correspondingly to each other in order to couple the template body and the coupling body to each other in an unambiguous and defined manner. In particular, an axial and/or non-rotatable coupling may be achieved, in dependence on a configuration of the coupling elements.

It is favorable if the first and second coupling elements are in engagement in a force- and/or positive-locking manner in the coupling position, and if they are completely separated from each other in a cleaning position. Thus the template body and the coupling body may be brought into engagement with each other and separated from each other again in a simple manner, in particular for cleaning purposes.

The instrumentarium may be configured in a simple manner if the first coupling element is configured in the form of a coupling element receptacle. In particular, the first coupling element may be arranged or formed on the coupling body.

It is favorable if the second coupling element is configured in the form of a coupling projection corresponding to the coupling element receptacle. Such a coupling projection may in particular be produced in a simple manner.

The coupling between the sawing template and the rasp body may in particular be further simplified if the coupling device defines a longitudinal axis, which in particular is defined by the first and/or second coupling element. For example, the second coupling element may be configured in the form of a coupling projection which defines the coupling longitudinal axis. The coupling projection may in particular be formed rotationally symmetrically in relation to the coupling longitudinal axis and/or the rotary axis.

The instrumentarium may be of particularly simple and compact configuration if the coupling longitudinal axis runs parallel or substantially parallel to the rotary axis.

The rotary axis preferably defines the coupling longitudinal axis. This configuration makes, in particular, the handling of the instrumentarium easier for a surgeon.

It is advantageous if the first and second coupling elements in the coupling position are non-rotatably coupled to each other. Thus a secure connection, optionally also without play, may be achieved between the sawing template and the rasp body.

In accordance with a further preferred embodiment, provision may be made for a first securing element of a securing device to be associated with the first coupling element, which first securing element in the coupling position is in engagement in a force- and/or positive-locking manner in a securing position with a second securing element arranged on the rasp body. In particular, the first securing element may be arranged in such a way that it acts in a direction which runs transversely to the coupling direction, i.e. transversely to the direction in which the first and second coupling elements may be brought into engagement with each other. It may thus be prevented in a simple manner that the sawing template and the rasp body are able to detach from each other in an undesired manner.

The sawing template and the rasp body may be secured to each other in the coupling position in a simple manner if the first and the second securing elements are configured in the form of cooperating latching members. The latter may, for example, automatically interengage and latch together when bringing the first and second coupling elements into engagement for securing a connection between the sawing template and the rasp body.

It is favorable if one of the two latching members is configured in the form of a latching projection and if the other one of the two latching members is configured in the form of a corresponding latching recess. A latching connecting device may thus be formed in a simple manner for securing the first and second coupling elements in engagement with each other in the coupling position.

It is advantageous if one of the two securing elements is arranged or formed on the first coupling element and if the other one of the two securing elements is arranged or formed on the second coupling element. Thus the instrumentarium may be of simple and compact configuration.

It is favorable if the latching projection is configured in such a way that, when bringing the first coupling element and the second coupling element into engagement, it is moved from a base position into a deflected position, and only when the coupling device adopts the coupling position is it able to engage into the latching recess from the deflected position, such that the securing device adopts the securing position. The first and second securing elements may thus latch to each other when the first and second coupling elements are brought into engagement with each other.

It is advantageous if the sawing template comprises two, three, four or more guide slots. This makes it possible, in particular, to use one single rasp body to prepare the femur bone, with which rasp body the bone cavity may be prepared for different prosthesis stems. Because the different prosthesis stems are also seated differently in the prepared cavity of the femur, a defined and, as the case may be, also correspondingly marked guide slot may be associated with each prosthesis stem. In this way, a number of required parts of the instrumentarium may be minimized. Thus a cleaning effort for the instrumentarium may be significantly reduced. In particular, the guide slots may be arranged or formed parallel or substantially parallel to each other.

Schematically depicted in FIGS. 1 to 3 is a first embodiment of a medical instrumentarium, designated as a whole with the reference numeral 10, for implanting a hip joint endoprosthesis. The instrumentarium comprises at least one sawing template 12 and optionally a rasp body 14 of a prosthesis rasp for preparing a cavity of a femur bone schematically depicted in FIG. 1, into which cavity a prosthesis stem of the hip joint endoprosthesis to be implanted is inserted.

The sawing template 12 comprises a first coupling element 18 for temporarily coupling the sawing template 12 to a second coupling element 20 of the rasp body 14 in a coupling position. The coupling position is schematically depicted for example in FIGS. 1, 2, and 11.

The first and second coupling elements 18 and 20 together form a coupling device 22. In the coupling position, the first and second coupling elements 18 and 20 are in engagement in a force- and/or positive-locking manner. In a cleaning position, as it is depicted schematically in FIG. 3, the first and second coupling elements 18 and 20 are completely separated from each other. Thus also the sawing template 12 and the rasp body 14 are completely separated from each other in the cleaning position.

The sawing template 12 comprises a coupling body 24 and a template body 26.

The first coupling element 18 is arranged or formed on the coupling body 24.

At least one guide slot 28 for a saw blade 30 of a surgical saw, which is not shown in more detail in the drawings, is arranged or formed on the template body 26. Two or more guide slots 28 may be provided on the template body 26. In the embodiment depicted schematically in FIGS. 1 to 3, a total of three guide slots 28 are arranged and formed, respectively.

Each guide slot 28 defines a guidance plane 32. Said guidance planes 32 run in particular parallel to each other in the embodiment of the template body 26 schematically depicted in FIGS. 1 to 3 and 12.

The instrumentarium 10 further comprises a coupling device 34 for temporarily coupling the coupling body 24 to the template body 26 in a coupling position. The coupling position is schematically depicted for example in FIGS. 1 and 2.

The coupling device 34 is configured in the form of a latching or snapping connecting device 36 and comprises first and second latching or snapping elements 38 and 40 which are in engagement with each other in the coupling position.

The coupling device 34 thus comprises first and second coupling elements 42 and 44, which form the latching or snapping elements 38 and 40.

The first and second coupling elements 42 and 44 are arranged or formed on the template body 26 on the one hand, namely the first coupling elements 42, and on the coupling body 24 on the other hand, namely the second coupling element 44. The first and second coupling elements 42 and 44 are in engagement in the coupling position in a force- and/or positive-locking manner.

The first coupling elements are configured in the form of coupling projections 46, namely as mounting brackets 50 which are concavely curved pointing toward a coupling longitudinal axis defined by the coupling device 22.

The coupling projections 46 are resiliently connected to the template body 26, for example by way of a connecting section 52 configured like a leaf spring.

As a whole, the template body 26 is configured as one piece. In addition, it is formed mirror-symmetrically to a symmetry plane 54 which runs perpendicularly to the guidance planes 32.

The coupling body 24 as a whole is formed substantially rotationally symmetrically with respect to the coupling longitudinal axis 48 and defines a grip region 56 which extends to a proximal end 58 of the coupling body 24.

A coupling recess 62 which corresponds to the coupling projection 56 is formed on the coupling body 24 adjacent to a distal end 60.

The coupling recess 62 is configured in the form of an annular groove 64 which is open pointing away from the coupling longitudinal axis 48. An outer diameter 66 of the coupling body 24 in the region of the annular groove 64 in a plane perpendicular to the coupling longitudinal axis 48 is slightly larger than an inner diameter 68, defined by the two mounting brackets 50, in a position in which the coupling body 24 and the template body 26 are separated from each other.

For coupling the coupling body 24 and the template body 26, the template body 26 is brought with the mounting brackets 50 up to the annular groove 64 in the direction of the arrow 70 with free ends 72 of the mounting brackets 50 in parallel to an insertion plane 74 defined by the annular groove 64. The ends 72 hereby slide on the cylindrical groove base surface 76 pointing away from the coupling body 24, such that the mounting brackets 50 are spread apart from each other. The connecting sections 52 hereby somewhat deform away from each other until the groove base surface 76 is able to abut against inner surfaces 78 of the mounting bracket 50 that point in the direction toward the coupling longitudinal axis 48. The connecting sections 52 hold the mounting brackets 50 somewhat under bias in the annular groove 64.

The described configuration of the coupling device 34 enables a rotation of the coupling body 24 and the template body 26 in the coupling position relative to each other about a rotary axis 80 defined by the coupling longitudinal axis 48.

In the embodiment of the instrumentarium 10 depicted in in Figures, the guidance planes 32 run transversely, in particular perpendicularly, to the rotary axis 80.

The first coupling element 18 is configured in the form of a coupling element receptacle 82. A free cross section of the coupling element receptacle 82 in a cut plane transverse to the coupling longitudinal axis 48, as depicted schematically in FIG. 10, is substantially rhombic.

The second coupling element 20 is formed on the rasp body 14 protruding from a proximal end face 84 thereof pointing in a proximal direction and defines a coupling projection 86. A cross sectional area 88 of the coupling projection 46 in a plane transverse to the coupling longitudinal axis 48 is composed of an isosceles triangle 90 and a semicircle 92, wherein a base of the triangle 90 defines a radius of the semicircle 92.

The coupling projection 86 is thus formed by a rotationally asymmetrical coupling pin 94 which in the coupling position is able to dip completely into the coupling element receptacle 82 on the coupling body 24, as is depicted for example in FIG. 11. As a result of the corresponding configuration of the coupling element receptacle 82 and the coupling projection 86, the first and second coupling elements 18 and 20 in the coupling position are non-rotatably in engagement with each other.

In order to secure the sawing template 12 on the rasp body 14 in the coupling position, a securing device 96 is provided which comprises a first securing element 98 that is associated with the first coupling element 18.

The first securing element 98 in a securing position is in engagement with a second securing element 100 in a force- and/or positive-locking manner. The second securing element 100 is arranged or formed, respectively, on the rasp body 14.

The securing element 98 is therefore arranged or formed on the first coupling element 80. The second securing element 100 is arranged or formed on the second coupling element 20. The second securing element 100 is configured in the form of a latching recess 102 on the coupling pin 94 and is open pointing in a direction transverse to the coupling longitudinal axis 48.

The first securing element 98 is configured in the form of a leaf spring bracket 104 with a latching nose 106 pointing in a direction toward the latching recess 102, which latching nose 106 in the securing position dips into the latching recess 102. This, however, is only possible when the coupling elements 18 and 20 adopt the coupling position.

The latching nose 106 forms a latching projection 108 which forms a first latching member 110. A second latching member 112 cooperating with the latter is formed by the latching recess 102.

The described configuration of the latching members 110 and 112 makes it possible in particular for the latching projection 108 to be moved, when bringing the first coupling element 18 and the second coupling element 20 into engagement, from a base position, as it is schematically depicted in FIG. 9, into a position deflected outwardly away from the coupling longitudinal axis 48, and only when the coupling device 22 adopts the coupling position is it able to move back from said deflected position and engage into the latching recess 102, such that the securing device 96 adopts the securing position in which the securing elements 98 and 100 are in engagement with each other in a force- and/or positive-locking manner.

The three guide slots 28 on the template body 26 are marked with letter combinations. The letter combinations "VAR", "STD", and "VLG" form abbreviations of the terms "Varus", "Standard", and "Valgus". The three guide slots 28 correspond to groove-shaped markings 114, 116 and to the end face 84 on the rasp body 14, which each define drive planes 118, 120, and 122 running parallel to each other.

When the rasp body 14 is driven into the cavity on the femur bone 16, the markings 114, 116 and the end face 84 thus define drive depths for the implant selected by the surgeon for the patient, namely the respective prosthesis stem. For a correction of a valgus position, a prosthesis stem is used that corresponds to the marking 114. For a standard prosthesis stem, the marking 116 is used. For correcting a varus position, the end face 84 is used. In this way, the femoral cavity may be prepared for three different prosthesis shapes with one single rasp body 14.

When the rasp body 14 is introduced into the femur bone 16 by driving by means of a handle that is not depicted and that is coupled to the second coupling element 20, then this handle may be removed and the second coupling element 20 may be coupled to the coupling body 24 in the described manner non-rotationally and axially in relation to the coupling axis 48.

In case the template body 26 is thereby not yet coupled to the coupling body 24, it may now be brought into engagement with the coupling body 24 in the manner described above. The surgeon may then resect the femur bone 16 with a saw so far that a femoral end face 126 is formed which is optimally adapted for the prosthesis stem to be inserted. For this purpose, the surgeon guides the saw blade 30 through the corresponding guide slot 28 and places the saw cut 124 on the femur bone 16. This is depicted for example in FIG. 1 for a prosthesis stem correcting a varus position. The saw blade 30 is guided through the guide slot 28 designated with "VAR" and a corresponding saw cut 120 is formed on the femur bone 16.

As a result of the rotatability of the template body 26 relative to the coupling body 24, a plurality of saw cuts 124 may be made from different directions.

When the femur bone 16 is provided with saw cuts 124 in the described manner, the sawing template 12 may again be removed from the rasp body 14. The rasp body 14 is then withdrawn from the femur bone 16. The femur bone 16 may then be further processed with the bone saw. The saw cuts 124 thereby serve as a guide for the saw blade 30 with which then the femur bone 16 is finally processed for forming the femoral end face 126.

A second embodiment of a template body 26' is schematically depicted in FIGS. 14 and 15. It corresponds in its structure to the template body 26. In particular the first coupling elements 42 for coupling the template body 26' to the coupling body 24 are of identical configuration.

The coupling body 26' differs from the coupling body 26 in the spacings of the guide slots 28'. Said template body 26' may in particular then be used when another rasp body 14 is used for preparing the femoral cavity, with which rasp body 14, for example, the femoral cavity is to be prepared for a "standard" prosthesis stem or for a prosthesis stem for correcting a "valgus" position or for a prosthesis stem for correcting a dysplastic malposition.

Therefore, the template body 26' may thus be coupled to the coupling body 24, in a manner analogous to how it is described above, for preparing the femur bone in connection with a further rasp body which differs from the rasp body 14 and is not depicted in the Figures.

Schematically depicted in FIGS. 16 to 18 is a second embodiment of an instrumentarium designated as a whole with the reference numeral 10". It comprises a coupling body 24" and a template body 26".

The coupling body 24" corresponds in its structure substantially to the coupling body 24. However, the annular groove 64" is laterally open pointing in the direction toward the end 58", though may be laterally delimited by a retaining ring 128" and thereby laterally closed.

The retaining ring 128" and the coupling body 24" may be connected to each other, in particular in a force- and/or positive-locking manner and/or by material bond. In particular, an annular set-back portion 130" may be formed on the coupling body adjacent to the annular groove 64", into which set-back portion 130" the retaining ring 128 engages when it laterally closes the annular groove 64".

The first coupling element 18" on the coupling body 24" is configured substantially identically to the first coupling element 18. Furthermore, associated with the first coupling element 18" is a first securing element 98" which is formed and arranged identically to the first securing element 98 on the first coupling element 18.

The coupling body 24" may thus be coupled to the rasp body 14 in a manner identical to how it is described above.

The template body 26" differs from the template body 26 substantially in the configuration of the second coupling element 44". The latter is configured in the form of a coupling ring 132" which is nearly closed in itself and which extends over at least 180° in circumferential direction in relation to the rotary axis 80" defined by the coupling longitudinal axis 48".

For coupling the template body 26" to the coupling body 24", the coupling ring 132" is pushed over the grip region 56" in the direction of the arrow 134" in parallel to the coupling longitudinal axis 48" until the coupling ring 132" is arranged surrounding the groove base surface 76".

Serving to secure the coupling ring 132" in the annular groove 64" is, as described, the retaining ring 128" which is likewise pushed in parallel to the arrow 134 over the grip region 56" coming from the end 58" and is brought up to the set-back portion 130" and fixed there. In particular, the retaining ring 128" may be welded, soldered, or bonded to the set-back portion 130".

The instrumentarium 10" further comprises an angle adjusting device 136" for adjusting an angular position of the coupling body 24" and the template body 26" in relation to the rotary axis 80" relative to each other. This is achieved in particular by the first and second coupling elements 42" and 44" being alignable relative to each other in discrete angular positions in relation to the rotary axis 80".

The angle adjusting device 136" comprises a plurality of first angle adjusting members 138" and at least one second angle adjusting member 140". The second angle adjusting member 140" is in engagement with different first angle adjusting members 138" in different angular positions.

The plurality of first angle adjusting members 138" is configured in the form of angle member recesses 142". The second angle adjusting member 140" is configured in the form of an angle adjusting projection 144".

The angle adjusting recesses 142" are arranged or formed on the second coupling element 44" and are open pointing in the direction toward the rotary axis 80". They form a kind of tooth arrangement on the coupling ring 132", which points in the direction toward the rotary axis 80".

The angle member projection 144" is resiliently formed or mounted, respectively, namely it forms a free end of a spring bracket 146" on the coupling body 24". The free end 148" projects outwardly, pointing away from the rotary axis 80", through a perforation 150" on the coupling body 24", such that the angle member projection 124" is able to dip into one of the angle member recesses 142".

When changing the angular position between the coupling body 24" and the template body 26" by rotating the same about the rotary axis 80", the spring bracket 146" is moved counter to a biasing force exerted by the same out of one of the angle member recesses 142" and, upon corresponding rotation, is moved back into an adjacent angle member recess 142" as a result of the biasing force stored in the spring bracket 146". Thus different numbers of angular positions may be defined as a result of corresponding size and width, respectively, of the angle member recesses 142" and the associated angle member projection 144".

The surgeon is also able to feel these different latchings when rotating the template body 26" about the rotary axis 80" relative to the coupling body 24".

The instrumentaria 10 and 10" described above may in particular be formed completely of metallic materials that can be sterilized by superheated steam.

A tooth arrangement similar to the angle member recesses 142" may selectively be provided on the mounting brackets 50 of the template body 26, such that a template body 26 modified in that way may optionally also be used together with the coupling body 24" for adjusting defined angular positions of the thusly modified template body and the coupling body 24" in relation to the rotary axis relative to each other.

REFERENCE NUMERAL LIST 10, 10" instrumentarium
12, 12" sawing template
14 rasp body
16 femur bone
18, 18" first coupling element
20 second coupling element
22 coupling device
24, 24" coupling body
26, 26', 26" template body
28, 28', 28" guide slot
30 saw blade
32 guidance plane
34, 34" connecting device
36 latching or snapping connecting device
38 first latching or snapping element
40 second latching or snapping element
42, 42" first coupling element
44, 44" second coupling element
46, 46" coupling projection
48, 48" coupling longitudinal axis
50, 50" mounting bracket
52 connecting section
54 symmetry plane
56, 56" grip region
58, 58" end
60 end
62, 62" coupling recess
64, 64" annular groove
66 outer diameter
68 inner diameter 70 arrow
72 end
74 insertion plane
76, 76" groove base surface
78 inner surface
80, 80" rotary axis
82, 82" coupling element receptacle
84 end face
86 coupling projection
88 cross sectional area
90 triangle
92 semicircle
94 coupling pin
96 securing device
98, 98" first securing element
100 second securing element
102 latching recess
104, 104" leaf spring bracket
106, 106" latching nose
108, 108" latching projection
110, 110" first latching member
112 second latching member
114 marking
116 marking
118 drive plane
120 drive plane
122 drive plane
124 saw cut
126 femoral end face
128" retaining ring
130" set-back portion
132" coupling ring
134" arrow
136" angle adjusting device
138" first angle adjusting member
140" second angle adjusting member
142" angle member recess
144" angle member projection
146" spring bracket
148" end
150" perforation

What is claimed is:

1. A medical instrumentarium for implanting a hip joint endoprosthesis, which instrumentarium comprises at least one sawing template with at least one guide slot for a saw blade, wherein:
   the sawing template comprises at least one first coupling element for temporarily coupling the sawing template to a second coupling element of a rasp body of a prosthesis rasp in a coupling position,
   the sawing template comprises a coupling body and a template body,
   the at least one first coupling element is arranged or formed on the coupling body,
   the at least one guide slot is arranged or formed on the template body,
   the medical instrumentarium further comprises a coupling device for temporarily coupling the coupling body and the template body in a coupling position, and
   the coupling device is configured in the form of a latching or snapping connecting device and comprises latching or snapping elements which are in engagement with each other in the coupling position.

2. The medical instrumentarium in accordance with claim 1, wherein:
   a) the medical instrumentarium further comprises a rasp body of a prosthesis rasp, which rasp body comprises a second coupling element of a coupling device comprising the first and the second coupling element, or
   b) the medical instrumentarium further comprises a rasp body of a prosthesis rasp, which rasp body comprises a second coupling element of a coupling device comprising the first and the second coupling element, wherein the first and second coupling elements are in engagement with each other in at least one of a force- and positive-locking manner in the coupling position, and they are completely separated from each other in a cleaning position.

3. The medical instrumentarium in accordance with claim 2, wherein the coupling device defines a coupling longitudinal axis which is defined in particular by at least one of the first and second coupling element.

4. The medical instrumentarium in accordance with claim 2, wherein the first and second coupling elements are non-rotatably coupled to each other in the coupling position.

5. The medical instrumentarium in accordance with claim 1, wherein:
   a) the first coupling element is configured in the form of a coupling element receptacle, or
   b) the first coupling element is configured in the form of a coupling element receptacle, wherein the second coupling element is configured in the form of a coupling projection corresponding to the coupling element receptacle.

6. The medical instrumentarium in accordance with claim 3, wherein:
   the coupling body and the template body in the coupling position are mounted on each other so as to be rotatable relative to each other about a rotary axis defined by the coupling device, and
   a) the coupling longitudinal axis runs parallel or substantially parallel to the rotary axis, or
   b) the rotary axis defines the coupling longitudinal axis.

7. The medical instrumentarium in accordance with claim 1, wherein a first securing element of a securing device is associated with the first coupling element, which first securing element in the coupling position is in engagement in at least one of a force- and positive-locking manner in a securing position with a second securing element arranged on the rasp body.

8. The medical instrumentarium in accordance with claim 7, wherein at least one of:
   a) the first and the second securing element are configured in the form of cooperating latching members, or the first and the second securing element are configured in the form of cooperating latching members, wherein one of the two latching members is configured in the form of a latching projection, and the other one of the two latching members is configured in the form of a corresponding latching recess, and
   b) one of the two securing elements is arranged or formed on the first coupling element, and the other one of the two securing elements is arranged or formed on the second coupling element.

9. The medical instrumentarium in accordance with claim 7, wherein the first and the second securing element are configured in the form of cooperating latching members, wherein one of the two latching members is configured in the form of a latching projection, and the other one of the two latching members is configured in the form of a corresponding latching recess, wherein the latching projection is configured in such a way that, when bringing the first coupling element and the second coupling element into engagement, it is deflected from a base position into a deflected position, and only when the coupling device adopts the coupling position is it able to engage into the latching recess from the deflected position, such that the securing device adopts the securing position.

10. The medical instrumentarium in accordance with claim 1, wherein the sawing template comprises two, three, four or more guide slots, wherein the guide slots are arranged or formed in parallel to each other.

11. The medical instrumentarium in accordance with claim 1, wherein:
 the coupling device comprises first and second coupling elements,
 the first and second coupling elements are arranged or formed on the coupling body on the one hand and on the template body on the other hand,
 the first and second coupling elements in the coupling position are in engagement in at least one of a force- and positive-locking manner, and
 the coupling body and the template body in the coupling position are mounted on each other so as to be rotatable relative to each other about a rotary axis defined by the coupling device.

12. A medical instrumentarium for implanting a hip joint endoprosthesis, which instrumentarium comprises at least one sawing template with at least one guide slot for a saw blade, wherein the sawing template comprises at least one first coupling element for temporarily coupling the sawing template to a second coupling element of a rasp body of a prosthesis rasp in a coupling position, wherein:
 the sawing template comprises a coupling body and a template body,
 the at least one first coupling element is arranged or formed on the coupling body,
 the at least one guide slot is arranged or formed on the template body,
 the medical instrumentarium further comprises a coupling device for temporarily coupling the coupling body and the template body in a coupling position,
 the coupling device comprises first and second coupling elements, the first and second coupling elements are arranged or formed on the coupling body on the one hand and on the template body on the other hand, and the first and second coupling elements in the coupling position are in engagement in at least one of a force- and positive-locking manner, and
 the coupling body and the template body in the coupling position are mounted on each other so as to be rotatable relative to each other about a rotary axis defined by the coupling device.

13. The medical instrumentarium in accordance with claim 12, wherein the first and second coupling elements are configured in the form of at least one coupling projection and in the form of a corresponding coupling recess.

14. The medical instrumentarium in accordance with claim 13, wherein at least one of:
 a) the at least one coupling projection is resiliently arranged or formed on the template body, and
 b) the at least one coupling projection is configured in the form of a mounting bracket which is concavely curved pointing toward the rotary axis, and
 c) the at least one coupling projection is configured in the form of a coupling ring which is closed in itself or extends over at least 180° in circumferential direction in relation to the rotary axis.

15. The medical instrumentarium in accordance with claim 13, wherein:
 a) the at least one coupling recess is configured in the form of an annular groove which is open pointing away from the rotary axis, and the at least one coupling projection in the coupling position engages at least in sections into the coupling recess in circumferential direction in relation to the rotary axis, or
 b) the at least one coupling recess is configured in the form of an annular groove which is open pointing away from the rotary axis, and the at least one coupling projection in the coupling position engages at least in sections into the coupling recess in circumferential direction in relation to the rotary axis, and wherein the annular groove is delimited laterally by a retaining ring, or
 c) the at least one coupling recess is configured in the form of an annular groove which is open pointing away from the rotary axis, and the at least one coupling projection in the coupling position engages at least in sections into the coupling recess in circumferential direction in relation to the rotary axis, and wherein the annular groove is delimited laterally by a retaining ring, and wherein the retaining ring and the coupling body are connected to each other in at least one of a force-locking manner and positive-locking manner and by material bond.

16. The medical instrumentarium in accordance with claim 12, wherein at least one of:
 a) the first and second coupling elements are alignable relative to each other in discrete angular positions in relation to the rotary axis, and
 b) the medical instrumentarium further comprises an angle adjusting device for adjusting an angular position of the coupling body and the template body in relation to the rotary axis relative to each other, or
 the medical instrumentarium further comprises an angle adjusting device for adjusting an angular position of the coupling body and the template body in relation to the rotary axis relative to each other, wherein the angle adjusting device comprises a plurality of first angle adjusting members and at least one second angle adjusting member, and the at least one second angle adjusting member is in engagement with different first angle adjusting members in different angular positions,
 the medical instrumentarium further comprises an angle adjusting device for adjusting an angular position of the coupling body and the template body in relation to the rotary axis relative to each other, wherein the angle adjusting device comprises a plurality of first angle adjusting members and at least one second angle adjusting member, and the at least one second angle adjusting member is in engagement with different first angle adjusting members in different angular positions, wherein the plurality of first angle adjusting members are configured in the form of angle member recesses, and the at least one second angle adjusting member is configured in the form of an angle member projection.

17. The medical instrumentarium in accordance with claim 12, wherein the medical instrumentarium further comprises an angle adjusting device for adjusting an angular position of the coupling body and the template body in relation to the rotary axis relative to each other, wherein the angle adjusting device comprises a plurality of first angle adjusting members and at least one second angle adjusting member, and the at least one second angle adjusting member is in engagement with different first angle adjusting members in different angular positions, wherein the plurality of first angle adjusting members are configured in the form of angle member recesses, and the at least one second angle adjusting member is configured in the form of an angle member projection, and wherein at least one of
  a) the angle member recesses are arranged or formed on the first or second coupling element and are arranged or formed pointing in the direction toward the rotary axis or away from the rotary axis
and
  b) the at least one angle member projection is resiliently mounted and, when changing the angular position by rotating the first and second coupling elements relative to each other about the rotary axis, is moved out of one of the angle member recesses counter to a biasing force and in another angular position is moved back into one of the angle member recesses as a result of the biasing force.

18. The medical instrumentarium in accordance with claim 12, wherein at least one of:
  a) the at least one guide slot defines a guidance plane which runs transversely, in particular perpendicularly, to the rotary axis, and
  b) the coupling body defines a grip region, and
  c) the grip region is formed symmetrically, in particular rotationally symmetrically, in relation to the rotary axis.

19. The medical instrumentarium in accordance with claim 12, wherein a first securing element of a securing device is associated with the first coupling element, which first securing element in the coupling position is in engagement in at least one of a force- and positive-locking manner in a securing position with a second securing element arranged on the rasp body.

20. The medical instrumentarium in accordance with claim 12, wherein:
  a) the medical instrumentarium further comprises a rasp body of a prosthesis rasp, which rasp body comprises a second coupling element of a coupling device comprising the first and the second coupling element, or
  b) the medical instrumentarium further comprises a rasp body of a prosthesis rasp, which rasp body comprises a second coupling element of a coupling device comprising the first and the second coupling element, wherein the first and second coupling elements are in engagement with each other in at least one of a force- and positive-locking manner in the coupling position, and they are completely separated from each other in a cleaning position.

21. A medical instrumentarium for implanting a hip joint endoprosthesis, which instrumentarium comprises at least one sawing template with at least one guide slot for a saw blade, wherein the sawing template comprises at least one first coupling element for temporarily coupling the sawing template to a second coupling element of a rasp body of a prosthesis rasp in a coupling position, wherein:
  the medical instrumentarium further comprises a rasp body of a prosthesis rasp, which rasp body comprises a second coupling element of a coupling device comprising the first and the second coupling element, and
  the first and second coupling elements are non-rotatably coupled to each other in the coupling position.

22. The medical instrumentarium in accordance with claim 21, wherein:
  the sawing template comprises a coupling body and a template body,
  the at least one first coupling element is arranged or formed on the coupling body, and
  the at least one guide slot is arranged or formed on the template body.

23. The medical instrumentarium in accordance with claim 22, further comprising a coupling device for temporarily coupling the coupling body and the template body in a coupling position.

24. The medical instrumentarium in accordance with claim 23, wherein:
  the coupling device comprises first and second coupling elements,
  the first and second coupling elements are arranged or formed on the coupling body on the one hand and on the template body on the other hand,
  the first and second coupling elements in the coupling position are in engagement in at least one of a force- and positive-locking manner, and
  the coupling body and the template body in the coupling position are mounted on each other so as to be rotatable relative to each other about a rotary axis defined by the coupling device.

25. The medical instrumentarium in accordance with claim 21, wherein a first securing element of a securing device is associated with the first coupling element, which first securing element in the coupling position is in engagement in at least one of a force- and positive-locking manner in a securing position with a second securing element arranged on the rasp body.

26. A medical instrumentarium for implanting a hip joint endoprosthesis, which instrumentarium comprises at least one sawing template with at least one guide slot for a saw blade, wherein:
  the sawing template comprises at least one first coupling element for temporarily coupling the sawing template to a second coupling element of a rasp body of a prosthesis rasp in a coupling position,
  the sawing template comprises a coupling body and a template body,
  the at least one first coupling element is arranged or formed on the coupling body,
  the at least one guide slot is arranged or formed on the template body,
  the medical instrumentarium further comprises a coupling device for temporarily coupling the coupling body and the template body in a coupling position, and
  the coupling device comprises first and second coupling elements, the first and second coupling elements are arranged or formed on the coupling body on the one hand and on the template body on the other hand, and the first and second coupling elements in the coupling position are in engagement in at least one of a force- and positive-locking manner.

27. The medical instrumentarium in accordance with claim 26, wherein:
  the coupling device comprises first and second coupling elements,
  the first and second coupling elements are arranged or formed on the coupling body on the one hand and on the template body on the other hand,
  the first and second coupling elements in the coupling position are in engagement in at least one of a force- and positive-locking manner, and
  the coupling body and the template body in the coupling position are mounted on each other so as to be rotatable relative to each other about a rotary axis defined by the coupling device.

28. A medical instrumentarium for implanting a hip joint endoprosthesis, which instrumentarium comprises at least one sawing template with at least one guide slot for a saw blade, wherein the sawing template comprises at least one first coupling element for temporarily coupling the sawing template to a second coupling element of a rasp body of a prosthesis rasp in a coupling position, wherein:
- a first securing element of a securing device is associated with the first coupling element, which first securing element in the coupling position is in engagement in at least one of a force- and positive-locking manner in a securing position with a second securing element arranged on the rasp body,
- the first and the second securing element are configured in the form of cooperating latching members.

29. The medical instrumentarium in accordance with claim 28, wherein:
- a) the medical instrumentarium further comprises a rasp body of a prosthesis rasp, which rasp body comprises a second coupling element of a coupling device comprising the first and the second coupling element, or
- b) the medical instrumentarium further comprises a rasp body of a prosthesis rasp, which rasp body comprises a second coupling element of a coupling device comprising the first and the second coupling element, wherein the first and second coupling elements are in engagement with each other in at least one of a force- and positive-locking manner in the coupling position, and they are completely separated from each other in a cleaning position.

30. A medical instrumentarium for implanting a hip joint endoprosthesis, which instrumentarium comprises at least one sawing template with at least one guide slot for a saw blade, wherein the sawing template comprises at least one first coupling element for temporarily coupling the sawing template to a second coupling element of a rasp body of a prosthesis rasp in a coupling position, wherein:
- a first securing element of a securing device is associated with the first coupling element, which first securing element in the coupling position is in engagement in at least one of a force- and positive-locking manner in a securing position with a second securing element arranged on the rasp body,
- one of the two securing elements is arranged or formed on the first coupling element, and
- the other one of the two securing elements is arranged or formed on the second coupling element.

* * * * *